United States Patent [19]

Beckage et al.

[11] Patent Number: 4,745,057
[45] Date of Patent: May 17, 1988

[54] METHOD, VECTORS AND TRANSFORMANTS FOR HIGH EXPRESSION OF HETEROLOGOUS POLYPEPTIDES IN YEAST

[75] Inventors: Cheryl A. Beckage; Thomas D. Ingolia, both of Indianapolis, Ind.

[73] Assignee: Eli Lilly and Company, Indianapolis, Ind.

[21] Appl. No.: 640,422

[22] Filed: Aug. 13, 1984

Related U.S. Application Data

[63] Continuation-in-part of Ser. No. 611,782, May 18, 1984.

[51] Int. Cl.$^4$ .............. C12P 21/00; C12P 19/34; C12N 15/00; C12N 5/00
[52] U.S. Cl. .................... 435/68; 435/70; 435/91; 435/172.3; 435/255; 435/320; 935/28; 935/37; 935/56; 935/60
[58] Field of Search .............. 435/68, 70, 91, 253, 435/317, 172.3, 255; 935/17, 28, 56, 60, 69, 37

[56] References Cited

FOREIGN PATENT DOCUMENTS 0060057 9/1982 European Pat. Off. .

OTHER PUBLICATIONS

Ingolia et al. (1982) *Molecular and Cellular Biology*, vol. 2, pp. 1388-1398.
Finkelstein et al. (1983) *Molecular and Cellular Biology*, vol. 3, pp. 1625-1633.
Urdea et al. (1983) *Proceedings National Academy Sciences, USA*, vol. 80, pp. 7461-7465.
Stepien et al. (1983) *Gene*, vol. 24, pp. 289-297.

*Primary Examiner*—Thomas G. Wiseman
*Assistant Examiner*—Stephanie Seidman
*Attorney, Agent, or Firm*—Mark R. Daniel; Leroy Whitaker

[57] ABSTRACT

Disclosed are a novel method for inducing the high expression of a nucleotide sequence which is under the transcriptional and translational control of the yeast YG100 gene and the novel vectors, transformants and selectable DNA for the practice thereof.

41 Claims, 4 Drawing Sheets

Restriction Site Map of Plasmids pIT210 and pIT3210 pIT210 pIT3210

Figure 1
Restriction Site Map of Plasmids pIT210 and pIT3210
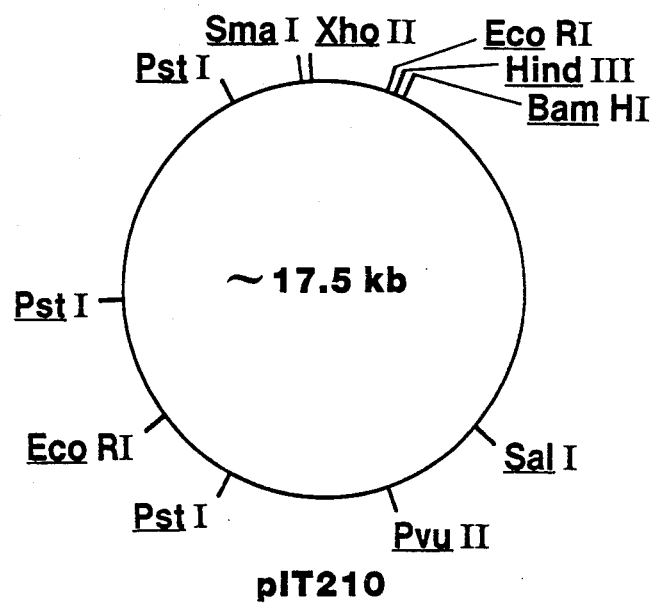
pIT210
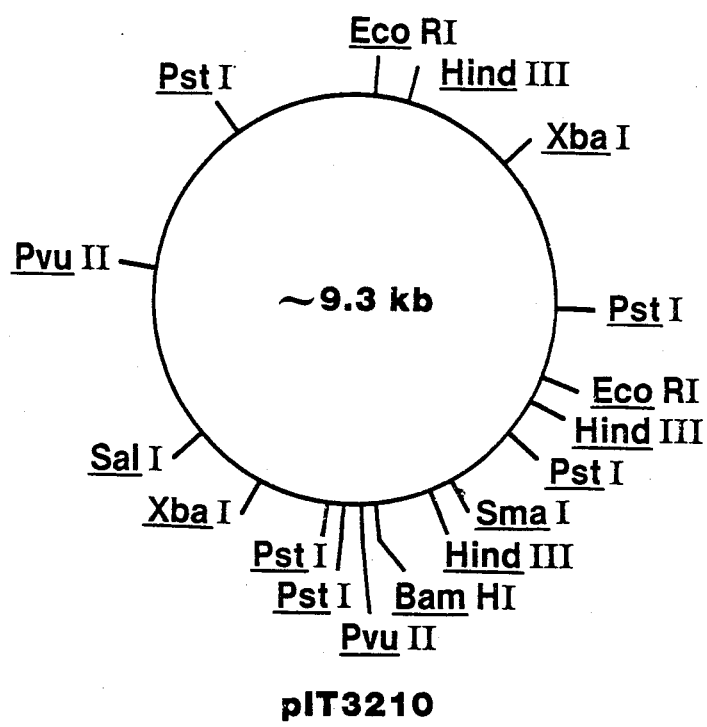
pIT3210

Effect of Cell Density on Induction**

Effect of Temperature on Induction

METHOD, VECTORS AND TRANSFORMANTS FOR HIGH EXPRESSION OF HETEROLOGOUS POLYPEPTIDES IN YEAST

CROSS REFERENCE

The present application is a continuation-in-part of copending U.S. patent application Ser. No. 611,782, filed May 18, 1984.

SUMMARY OF THE INVENTION

The present invention is a novel method for inducing high level expression of a nucleotide sequence that codes for a heterologous polypeptide. Such method comprises transforming a yeast cell with DNA that comprises, in translational reading frame, the transcriptional and translational activating sequence of the yeast YG100 gene and a nucleotide sequence that codes for a bioactive polypeptide. After aerobic culturing, the transformed yeast cell is subjected first to anaerobic and then to aerobic culture conditions. Recovery from anoxic conditions and also culturing at appropriate temperatures at or near stationary growth phase induces the yeast YG100 transcriptional activating sequence and thus results in the high expression of product. The invention further comprises recombinant DNA expression vectors and transformants required to use the aforementioned method.

The development and exploitation of recombinant DNA technology in yeast has been limited by the general paucity of vectors and methods for high level gene expression. Although the PGK (Dobson et al., 1982, Nucleic Acids Research 10:2625), LEU2 (Casadaban et al., 1983, Methods in Enzymology 100(B):293), HIS (Donahue et al., 1982 Gene 18:47; Silverman et al., 1982, Mol. Cellul. Bio. 2:1212), and ADH (Russell et al., 1983, J. Biol. Chem. 258:2674) promoter systems are known, few, if any, other DNA sequences and methods are available for driving the expression in yeast of heterologous polypeptides. The present invention helps alleviate this problem by providing a method for inducing high levels of gene expression and therefore represents a significant advance in the technical art.

For purposes of the present invention as disclosed and claimed herein, the following terms are as defined below.

Recombinant DNA Expression Vector—any agent capable of autonomous replication or genomic integration, including but not limited to plasmids, comprising a DNA molecule into which one or more transcriptional and translational activating sequence(s) have been incorporated.

Transcriptional Activating Sequence—any DNA sequence that provides for the transcription of DNA into a mRNA transcript.

Translational Activating Sequence—any DNA sequence that provides for the translation of a mRNA transcript into a peptide or polypeptide.

Translational Start Signal—any DNA triplet that codes for a translational start codon.

Translational Stop Signal—any DNA triplet that codes for a translational stop codon.

Transformation—the introduction of DNA into a recipient host cell that changes the genotype.

Transformant—a recipient host cell that has undergone transformation.

Restriction Fragment—any linear DNA generated by the action of one or more restricton enzymes.

Replicon or Origin of Replication—any DNA sequence that controls the replication of recombinant DNA cloning and expression vectors.

Functional Polypeptide—a recoverable bioactive heterologous polypeptide or precursor, a recoverable bioactive polypeptide comprising a heterologous polypeptide and a portion or whole of a homologous polypeptide, or a recoverable bioinactive fusion polypeptide comprising a heterologous polypeptide and a bioinactivating polypeptide which can be specifically cleaved.

Fused Gene Product—a recoverable heterologous polypeptide which comprises a portion or whole of a homologous polypeptide.

DESCRIPTION OF THE FIGURES

FIG. 1—restriction site map of plasmids pIT210 and pIT3210.

DETAILED DESCRIPTION OF THE INVENTION

Figure 2:
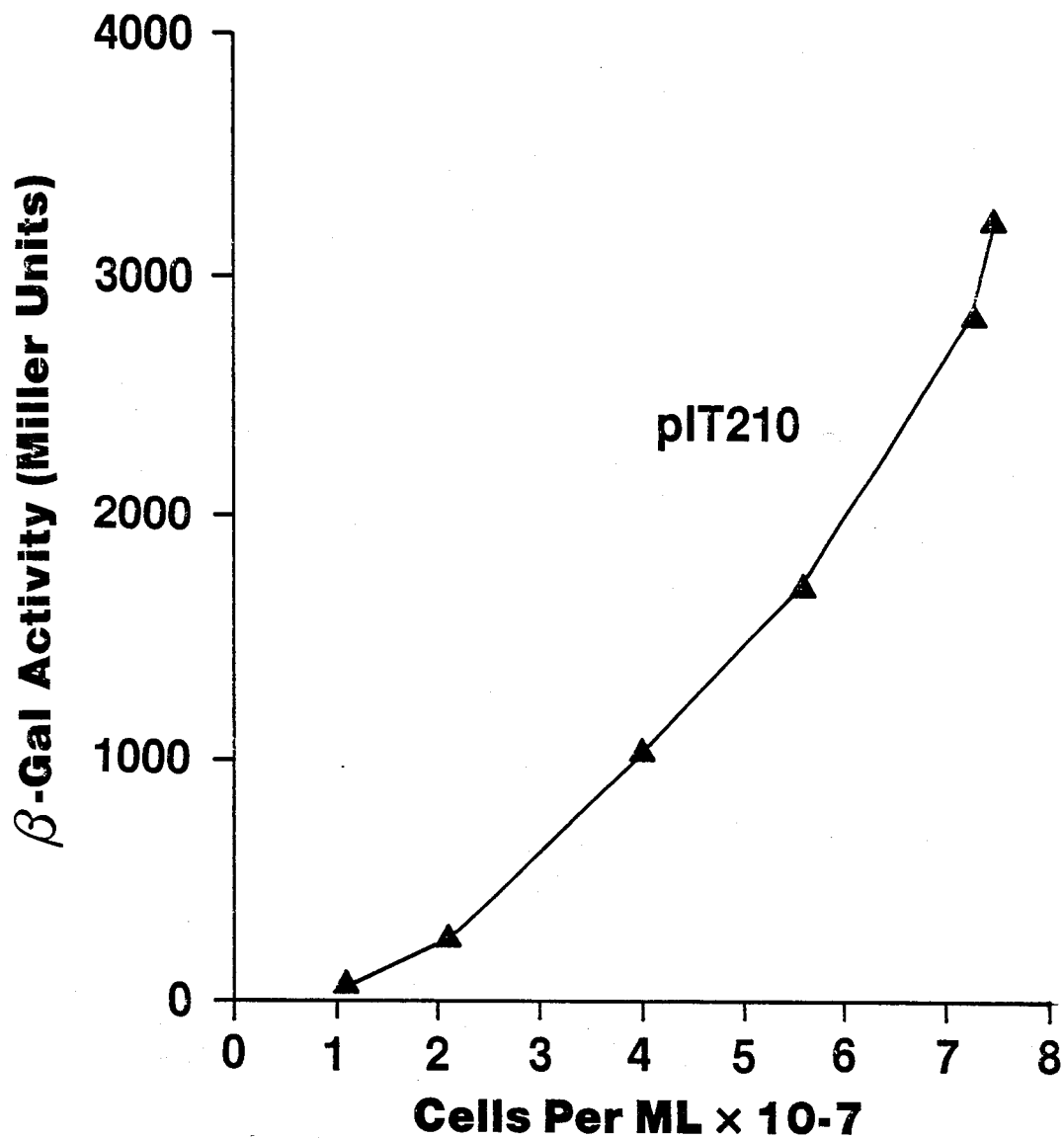
FIG. 2—effect of cell density on induction of YG100 transcriptional and translational activating sequence.

The present invention comprises a method for inducing high level expression in yeast of a nucleotide sequence that is under the transcriptional and translational control of the yeast YG100 gene, said method comprising (1) transforming a yeast cell with selectable DNA that is capable of autonomous replication or genomic integration, said DNA comprising, in translational reading frame,
  (a) the transcriptional and translational activating sequence of the yeast YG100 gene, and
  (b) a nucleotide sequence that codes for a functional heterologous polypeptide,
(2) culturing said transformed cell under conditions suitable for aerobic growth,
(3) culturing said aerobically-grown cell under conditions suitable for anaerobic growth, and
(4) culturing said anaerobically-grown cell under conditions suitable for aerobic growth and gene expression, subject to the limitation that said conditions for anaerobic growth are maintained for a time sufficient to cause induction when said conditions for aerobic growth are restored.

The invention further comprises recombinant DNA expression vectors and transformants employed to practice the aforementioned method.

The present invention can be constructed by ligating the ~1.3 kb BglII-BamHI fragment of plasmid pIT120 into BamHI-digested plasmid pMC1587. Plasmid pIT120 contains the transcriptional and translational activating sequence of the yeast YG100 gene and can be obtained from *E. coli* K12 JA221/pIT120, a strain deposited and made part of the permanent stock culture collection of the Northern Regional Research Laboratory, Peoria, Ill. The strain is available as a preferred source and stock reservoir of the plasmid under the accession number NRRL B-15603 The plasmid pMC1587 starting material contains the pBR322 replicon, an ampicillin resistance gene, sequences from the yeast 2 micron DNA, the LEU2 gene and a modified *E. coli* lac operon containing a BamHI site in the coding information for the eighth amino acid of the lacZ gene. The plasmid can be obtained from *E. coli* K12 JA221/pMC1587, a strain deposited and made part of the permanent stock culture collection of the Northern Regional Research Laboratory, Peoria, Ill. The strain is available as a preferred source and stock reservoir of the plasmid under the accession number NRRL B-15442.

The ~1.3 kb BglII-BamHI fragment of plasmid pIT120 contains the aforementioned transcriptional and translational activating sequence and also a portion of the coding sequence of the YG100 gene. The translational reading frame at the BamHI site of the ~1.3 kb fragment is the same as that found at the BamHI site of the truncated beta-galactosidase gene in plasmid pMC1587. Therefore, ligation (in the proper orientation) of the aforementioned ~1.3 kb BglII-BamHI fragment into the BamHI site of pMC1587 results in a plasmid that codes for a YG100-lacZ fused gene product. The resultant plasmid, designated herein as plasmid pIT210, is ~17.5 kb and can be used for purposes of the present invention. A restriction site map of plasmid pIT210 is presented in FIG. 1 of the accompanying drawings.

Additional plasmids that further exemplify the present method can also be constructed. For example, ligation of the ~0.21 kb XbaI-TaqI and ~7 kb XbaI-BamHI fragments of plasmid pIT120, the ~0.25 kb HphI-BamHI fragment of plasmid pNM587.4-4 and the linker sequence

```
CGAGAAGGGATTGAGTTGTAGTTTCGTTTCCCAATTCTTAC
||||||||||||||||||||||||||||||||||||||||
TCTTCCCTAACTCAACATCAAAGCAAAGGGTTAAGAATG

TTAAGTTGTTTTATTTTCTCTATTTGTAAGATAAGCACATC
||||||||||||||||||||||||||||||||||||||||
AATTCAACAAAATAAAAGAGATAAACATTCTATTCGTGTAG

AAAAGAAAAGTAATCAAGTATTACAAGAAACAAAAATTCAA
||||||||||||||||||||||||||||||||||||||||
TTTTCTTTTCATTAGTTCATAATGTTCTTTGTTTTAAGTT

GTAAATAACAGATAATATGTTCGTTAACCAACACTTGT
||||||||||||||||||||||||||||||||||||||
CATTTATTGTCTATTATACAAGCAATTGGTTGTGAAC
``` wherein
A is deoxyadenyl,
G is deoxyguanyl,
C is deoxycytosyl and
T is thymidyl,
results in the intermediate plasmid pIT2210. The plasmid pNM587.4-4 starting material can be obtained from *E. coli* K12 JA221/pNM587.4-4, a strain deposited and made part of the permanent stock culture collection of the Northern Regional Research Laboratory Peoria, Ill. The strain is available as a source and stock reservoir of the plasmid under the accession number NRRL B-15812. The ~1.6 kb BamHI-BglII fragment of plasmid pIT2210 contains the yeast YG100 gene transcriptional and translational activating sequence fused with a nucleotide sequence that codes for human proinsulin. Ligation of the aforementioned fragment into BamHI-digested plasmid YEp24 results in the bifunctional illustrative plasmid pIT3210. Plasmid YEp24, also known as pRB5, has been deposited without restriction and is publicly available from the American Type Culture Collection, Rockville, Md. 20852 under the accession number ATCC 37051. Illustrative plasmid pIT3210 is ~9.3 kb and comprises, in addition to the yeast YG100 transcriptional and translational activating sequence fused with a coding sequence for human proinsulin, the origin of replication and ampicillin resistance gene of plasmid pBR322, the URA3 gene from yeast and the replication sequence from the yeast 2 micron plasmid. The plasmid codes for the expression of human proinsulin and is useful for further exemplifying the present invention. A restriction site map of plasmid pIT3210 is presented in FIG. 1 of the accompanying drawings.

Both of the illustrative pIT210 and pIT3210 plasmids can be used to transform yeast cells following variations of conventional procedures. Best results for inducing the YG100 transcriptional and translational activating sequence are obtained (1) by first culturing the transformed yeast cells under conventional aerobic conditions until about mid-logarithmic growth phase; (2) subjecting the aerobically-grown cells to anaerobic culture conditions for about 12 hours to at or near stationary growth phase; and (3) subjecting the anaerobically-grown cells to conventional aerobic culture conditions. Recovery from anaerobiosis (anoxic conditions) greatly induces the YG100 transcriptional and translational activating sequence which in turn leads to high levels of gene expression. In the case of plasmids pIT210 and pIT3210, such induction results respectively in the high level expression of beta-galactosidase and human proinsulin.

The yeast YG100 transcriptional activating sequence can be further induced by growing YG100 sequence-containing cells at late growth phase. More particularly, culturing cells transformed by plasmid pIT210 at stationary phase results in the strong induction and high level expression of beta-galactosidase activity. Thus, as shown in FIG. 2 of the accompanying drawings, as *Saccharomyces cerevisiae*/pIT210 cells reach the maximum cell density of $8 \times 10^7$ cells/ml in conventional minimal media (0.67% yeast nitrogen base without amino acids, 2% glucose plus auxotrophic requirements), the beta-galacotosidase level increases dramatically. High expression of human proinsulin can also be obtained when yeast cells transformed by plasmid pIT3210 are similarly cultured at late growth phase. Skilled artisians will readily appreciate that maximum induction is best achieved by subjecting transformed cells to both of the aforementioned culture conditions, i.e. recovery from anoxia and culturing at or near stationary growth phase.

Figure 4:
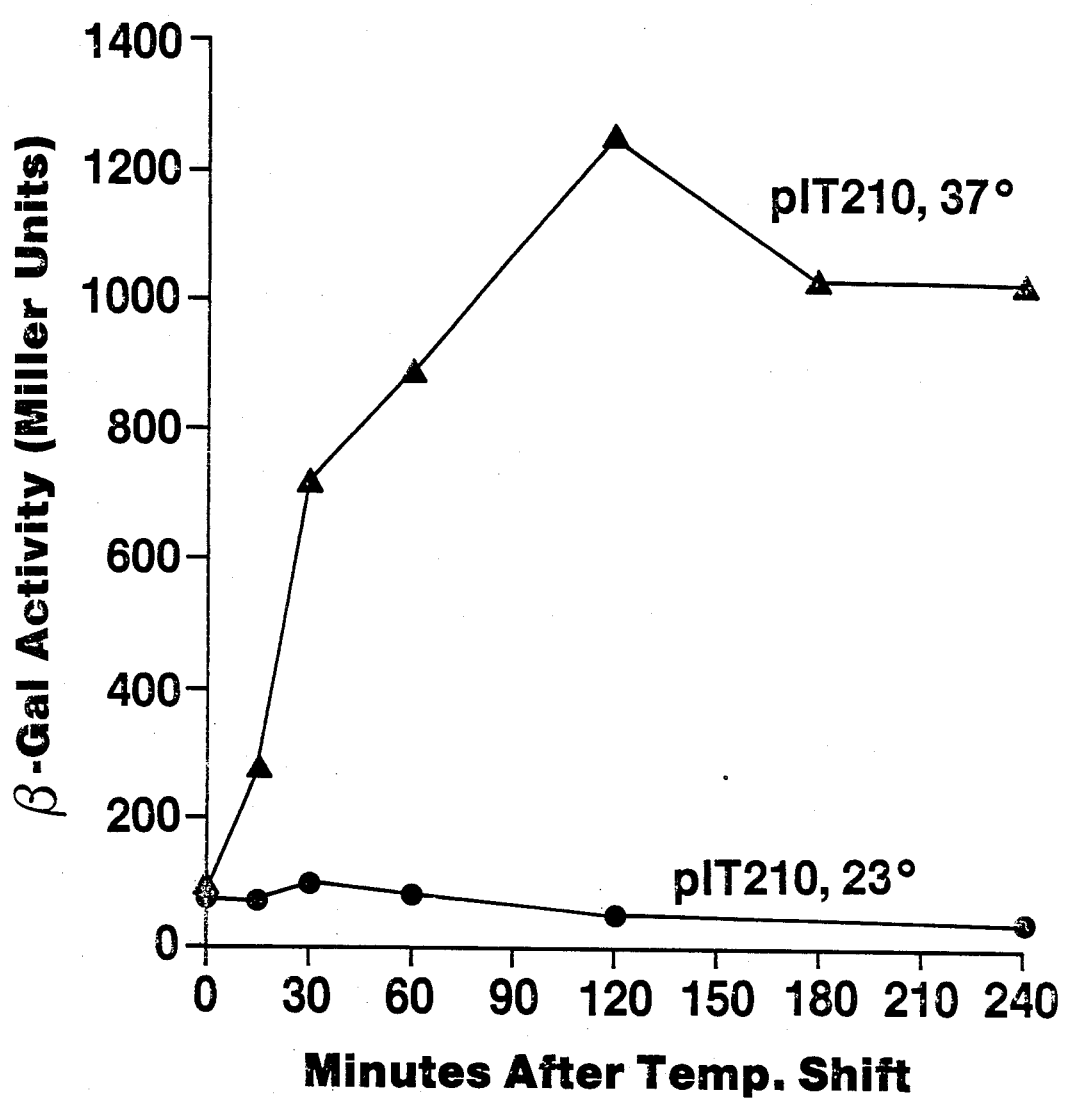
FIG. 4—effect of temperature on induction of YG100 transcriptional and translational activating sequence.

The effectiveness of one set of inducing conditions, such as recovery from anoxia, is not eliminated or masked by a previous induction resulting from culturing at late growth phase. In addition, cells induced at high cell density also accumulate more activity when further stimulated by culture temperatures of about 37° C. For example, *Saccharomyces cerevisiae*/pIT210 cells grown to stationary phase for about 16 hours at a chronic 37° C. accumulated 10,170 units of beta-galactosidase, a level about 3 or 4 fold higher than that accumulated by cells at either 23° or 30° C. The extent of induction of the YG100 transcriptional and translational activating sequence by increases in temperature, as shown in FIG. 4 of the accompanying drawings, can be even more dramatic. For example, after a temperature shift from 23° to 37° C., a new level of beta-galactosidase expression is reached after about 60 minutes which is at least 20 fold higher than the previous expression level. The calculated level of induction is even higher, up to 50 fold when the variable but finite amount of nonspecific hydrolytic activity in the control (untransformed) yeast cells is taken into account. Thus, combinations of inducing conditions, for example, the aforementioned recovery from anoxia, culturing at late growth phase and increased culture temperature, greatly enhances induction and results in the highest levels of heterologous gene expression. Such combinations are therefore preferred for purposes of the present invention.

The method of the present invention is in no way limited to the use of autonomously replicating vectors. Although replication in the illustrative plasmids pIT210 and pIT3210 is autonomous and controlled by the replication sequence of the yeast 2 micron plasmid, vectors which integrate into the yeast cell genome can also be constructed. One such integrative vector is the illustrative beta-galactosidase encoding plasmid pIT2100. Such vectors are constructed by cloning the yeast YG100 transcriptional and translational activating sequence into one of a number of known integrating vectors which include, but are not limited to, plasmids YIp1, YIp5 and YIp25 to 33 (Botstein et al., 1979, Gene 8:17). In addition, almost any vector can be made to integrate by the incorporation of genomic DNA from the host cell into which the vector is to be inserted. Thus, yeast cells transformed with yeast genomic DNA-containing vectors undergo homologous recombination resulting in integration of heterologous DNA associated with the genomic sequences. A plethora of both autonomously replicating and integrating vectors can therefore be used for cloning the YG100 transcriptional and translational activating sequence for purposes of the present invention. A detailed construction protocol for illustrative integrating plasmid pIT2100 is presented in Example 5 below.

The present invention is highly versatile such that virtually any nucleotide sequence that codes for a functional polypeptide can be substituted for the beta-galactosidase and human proinsulin coding sequences exemplified above. Such coding sequences include, but are not limited to, sequences that code for bovine growth hormone (bGH), bovine pre-growth hormone, human growth hormone (hGH), human pre-growth hormone (pre-hGH), porcine growth hormone (pGH), mammalian growth hormone, avian growth hormone, growth hormone releasing factor, human insulin A chain, human insulin B chain, human pre-proinsulin, human and non-human interferon, urokinase, tissue plasminogen activator, interleukin I, interleukin II, any hormone, any enzyme and any bioactive polypeptide of research or commercial value.

The method and vectors of the present invention can be used in a wide array of *Saccharomyces cerevisiae* host organisms, such use not being limited by the yeast DBY746 and DBY689 strains specifically exemplified. Both strains can be obtained for a nominal fee from the Yeast Genetic Stock Center, Berkeley, Calif. 94720. In addition, yeast strain DBY746 can also be obtained from the American Type Culture Collection, Rockville, Md. 20852. Other yeast strains which can be substituted for the aforementioned strains include, but are not limited to, yeast strains X4003-5B, DBY747, SHY-1, SHY-2, SHY-3, and SHY-4. The above strains are well known and can also be obtained from the Yeast Genetic Stock Center. Although all of the embodiments of the present invention are useful, some of the vectors and transformants are preferred. Preferred embodiments include plasmid pIT210 and transformants *Saccharomyces cerevisiae* DBY689/pIT210 and *S. cerevisiae* DBY746-/pIT210.

Those skilled in the art will recognize that the method and related expression vectors of the present invention are used to produce a heterologous polypeptide by means of fermentation. The heterologous protein product is isolated and purified from the resulting fermentation broth by routine methods well known in the art. The following examples further illustrate the invention disclosed herein. Both an explanation and the actual procedures for making and using the invention are described where appropriate.

EXAMPLE 1.

Preparation of Plasmid pIT210 and *E. coli* K12 JA221/pIT210

A. Isolation of Plasmid pIT120

The bacterium *E. coli* K12 JA221/pIT120 (NRRL B-15603) was cultured in TY broth (1% tryptone, 0.5% yeast extract, 1% sodium chloride, pH 7.4) with 50 μg/ml of antibiotic ampicillin according to conventional microbiological procedures. After 18 hours incubation, about 0.5 ml of the culture was transferred to a 1.5 ml Eppendorf tube and centrifuged for about 15 seconds. Unless otherwise indicated, all the manipulations were done at ambient temperature. The resultant supernatant was carefully removed with a fine-tip aspirator and the cell pellet was suspended in about 100 μl of freshly prepared lysozyme solution containing 2 μg/ml lysozyme, 50 mM glucose, 10 mM CDTA (cyclohexane diaminetetracetate) and 25 mM Tris-HCl, pH 8. After incubation at 0° C. for 30 minutes, about 200 μl of alkaline SDS (sodium dodecyl sulfate) solution (0.2N NaOH, 1% SDS) were added. The tube was gently vortexed and then maintained at 0° C. for 15 minutes. Next, about 15 μl of 3M sodium acetate (prepared by dissolving 3 moles of sodium acetate in a minimum of water, adjusting the pH to 4.8 with glacial acetic acid and then adjusting the volume to 1 l.) were added and the contents of the tube mixed gently by inversion.

The tube was maintained at 0° C. for 60 minutes and then centrifuged for 5 minutes to yield an almost clear supernatant. About 0.3 ml of the supernatant were transferred to a second centrifuge tube to which 1 ml of cold ethanol was added. After the tube was held at −20° C. for 30 minutes, the resultant precipitate was collected by centrifugation and the supernatant removed by aspiration. The resultant pellet was dissolved in 100 μl of 0.1M sodium acetate/0.05M Tris-HCl (pH 8) and then conventionally re-precipitated by the addition of 2 volumes of cold ethanol. The resultant precipitate was collected by centrifugation and constituted the desired plasmid pIT120 DNA. Plasmid pIT120 was dissolved in 20 μl of TE buffer (10mM Tris-HCl, pH8, 1 mM EDTA) and stored at 0° C. for future use.

B. Isolation of Plasmid pMC1587

The desired isolation was carried out in substantial accordance with the teaching of Example 1A except that *E. coli* K12 JA221/pMC1587 (NRRL B-15442), rather than *E. coli* K12 JA221/pIT120, was used. The desired plasmid pMC1587 was dissolved in 20 μl of TE buffer and stored at 0° C. for future use.

Construction of the ~1.3 kb BglII-BamHI Fragment of Plasmid pIT120

About 5 μl (5 μg) of plasmid pIT120 (isolated in Example 1A) in TE buffer (10mM Tris-HCl, pH 8, 1 mM EDTA), 5 μl DTT (100 mM Dithiothreitol), 5 μl (1000 mg/ml) BSA (bovine serum albumin), 25 μl water, 2.5 μl (5 units) BglII restriction enzyme, 2.5 μl (5 units) BamHI restriction enzyme and 5 μl 10X reaction mix* were incubated at 37° C. for about 1 hour. The reaction was terminated by incubation at 70° C. for 5 minutes. The mixture was then cooled on ice, extracted with each of phenol and chloroform:isoamyl alcohol (24:1) and then ethanol precipitated. The desired ~1.3 kb BglII-BamHI restriction fragments were conventionally separated and isolated by agarose gel electrophoresis (Maniatis et al., 1982, Molecular Cloning, Cold Spring Harbor Laboratory, Cold Spring Harbor, N.Y.). The desired μ1.3 kb fragments were dissolved in about 20 μl of TE buffer and stored at 0° C.

*Reaction mix (10X) for BglII restriction enzyme was prepared with the following composition:
600 mM NaCl
100 mM Tris-HCl, pH 7.4
100 mM MgCl$_2$

D. BamHI Digestion of Plasmid pMC1587

About 5 μl (5 μg) of plasmid pMC1587 (isolated in Example 1B) in TE buffer, 5 μl DTT (100 mM Dithiothreitol), 5 μl (1000 mg/ml) BSA (bovine serum albumin), 25 μl water, 5 μl (5 units) BamHI restriction enzyme and 5 μl 10X reaction mix* were incubated at 37° C. for about 1 hour. The reaction was terminated by incubation at 70° C. for 5 minutes. After cooling, the resultant digest was extracted with each of phenol and chloroform:isoamyl alcohol (24:1) and then ethanol precipitated. The desired ~16.8 kb BamHI fragments were dissolved in about 20 μl of TE buffer and stored at 0° C.

*Reaction mix (10X) for BamHI restriction enzyme was prepared with the following composition:
500 mM NaCl
100 mM Tris-HCl, pH 7.5
100 mM MgCl$_2$

E. Ligation and Final Construction of *E. coli* K12 JA221/pIT210

About 1 μl (1 μg) of the pMC1587 BamHI digest was mixed with 1 μl (1 μg) of the ~1.3 kb BglII-BamHI fragment of plasmid pIT120, 37 μl water, 5 μl (10 mM) ATP, 5 μl ligation mix* and 1 μl T4 DNA ligase (~10$^5$ New England Bio Lab. Units). The mixture was incubated at 16° C. for about 16 hours and then the reaction was terminated by incubation at 70° C. for 5 minutes. After cooling on ice, the resultant ligation mixture was used to transform, in substantial accordance with the transformation procedure of Wensink, 1974, Cell 3:315, *E. coli* K12 JA221 on TY plates containing 50 μg/ml of antibiotic ampicillin. Bacterial strain *E. coli* K12 JA221 has been deposited and made part of the permanent stock culture collection of the Northern Regional Research Laboratory, Peoria, Ill. It is available to the public under the accession number NRRL B-15211. The desired transformant, designated herein as *E. coli* K12 JA221/pIT210, was conventionally identified, characterized and cultured using standard microbiological techniques (See Example 7E), and then used to isolate plasmid pIT210 in substantial accordance with the procedure of Example 1A. A restriction site and functional map of plasmid pIT210 is shown in FIG. 1 of the accompanying drawings.

*Ligation mix was prepared with the following composition:
500 mM Tris-HCl, pH 7.8
200 mM Dithiothreitol
100 mM MgCl$_2$

EXAMPLE 2

Construction of *Saccharomyces cerevisiae*/pIT210

The desired transformation of yeast cells was carried out using yeast protoplasts in substantial accordance with the teaching of Hinnen et al., 1978, Proc. Natl. Acad. Sci. USA 75:1929 with minor modifications. Assuming sterile conditions and a culture volume of 100 ml, *Saccharomyces cerevisiae* DBY746 (ATCC 44773 and also available from the Yeast Genetic Stock Center, Berkeley, Calif. 94720) was first grown in YPD (1% Bacto-Yeast Extract, 2% Bacto-Peptone, 2% Glucose) to an A600 of about 1.0 and then washed in 15 ml of 1.2M sorbitol. After suspension in another 15 ml volume of 1.2M sorbitol, about 100 μl of 2.5 mg/ml zymolase 60,000 (prepared by suspending the zymolase in 5 mM KPi; pH 7.6 and 1.2 M sorbitol) were added. The suspension was incubated at room temperature and the extent of protoplasting monitored by suspending 20 μl aliquots in 180 μl of 10% SDS and observing under a phase contrast microscope. Protoplasts appear black under phase contrast in SDS solution. When protoplasting was about 90% complete, the protoplasts were washed twice in 15 ml of 1.2 M sorbitol, collected with as little g force as possible and resuspended gently in 600 μl of YPD containing 1.2 M sorbitol, 10 mM calcium chloride and 10 mM Tris-HCl, pH 7.5.

Transformation was carried out by adding about 20 μl of plasmid pIT210 DNA to 0.2 ml aliquots of the protoplast suspension. The resultant mixture was incubated at room temperature for 10 minutes and then, after addition of 1 ml of 20% PEG 3350 (polyethyleneglycol), 10 mM calcium chloride and 10 mM Tris-HCl, pH 7.5, incubated again for 60 minutes. Different volumes of the transformed protoplasts were plated in 25 ml of 3% regeneration agar containing required nutrients*. The agar was stored in a water bath at 45° to 50° C. before plating and, after solidification, the plates were incubated at 30° C. for 48 to 72 hours. The resultant colonies were conventionally cultured and constituted the desired *Saccharomyces cerevisiae*/pIT210 transformants.

*Regeneration agar was prepared with the following composition:
0.67% yeast nitrogen base without amino acids (obtained from Difco)
3% agar
1.2 M sorbitol
Conventional required nutrients (except for marker on plasmid); drop out solids are particularly useful.

EXAMPLE 3

Incubation of *Saccharomyces cerevisiae*/pIT210 Under Anaerobic and Aerobic Conditions

*Saccharomyces cerevisiae*/pIT210 cells were subjected to anaerobic conditions by incubation in a GasPak 100 Anaerobic System (BBL Microbiology Systems Cockeysville, Md., Seip and Evans, 1980, J. Cl. Microbiol.

11:226). Those skilled in the art will understand that other anaerobic culture systems can also be employed and that anaerobic conditions can be attained by conventional large scale yeast fermentation without infusion of oxygen.

About 20 ml of exponentially growing cells in a sterile 250 ml beaker containing a magnetic stirring bar and thermometer were placed into the anaerobic chamber. After sealing, the chamber was placed on a magnetic stirring plate and the cells incubated for about 12 hours with vigorous stirring. Proper functioning of the Gas-Pak system was initially monitored by appearance of a condensate on the walls of the chamber and an increase in the temperature of the lid near the catalyst. Attainment of anaerobiosis was monitored by the loss of color of a methylene blue indicator.

After subjection to anaerobic culture conditions for about 12 hours, the culture chamber was opened and normal atmospheric oxygen levels restored. The cells were then conventionally cultured under aerobic conditions for at least an additional 30 minutes. The result was a strong induction of the YG100 gene transcriptional and translational activating sequence and the concommitant high level expression of beta-galactosidase activity.

EXAMPLE 4

Measurement of Beta-Galactosidase Activity in *Saccharomyces cerevisiae*/pIT210

Figure 3:
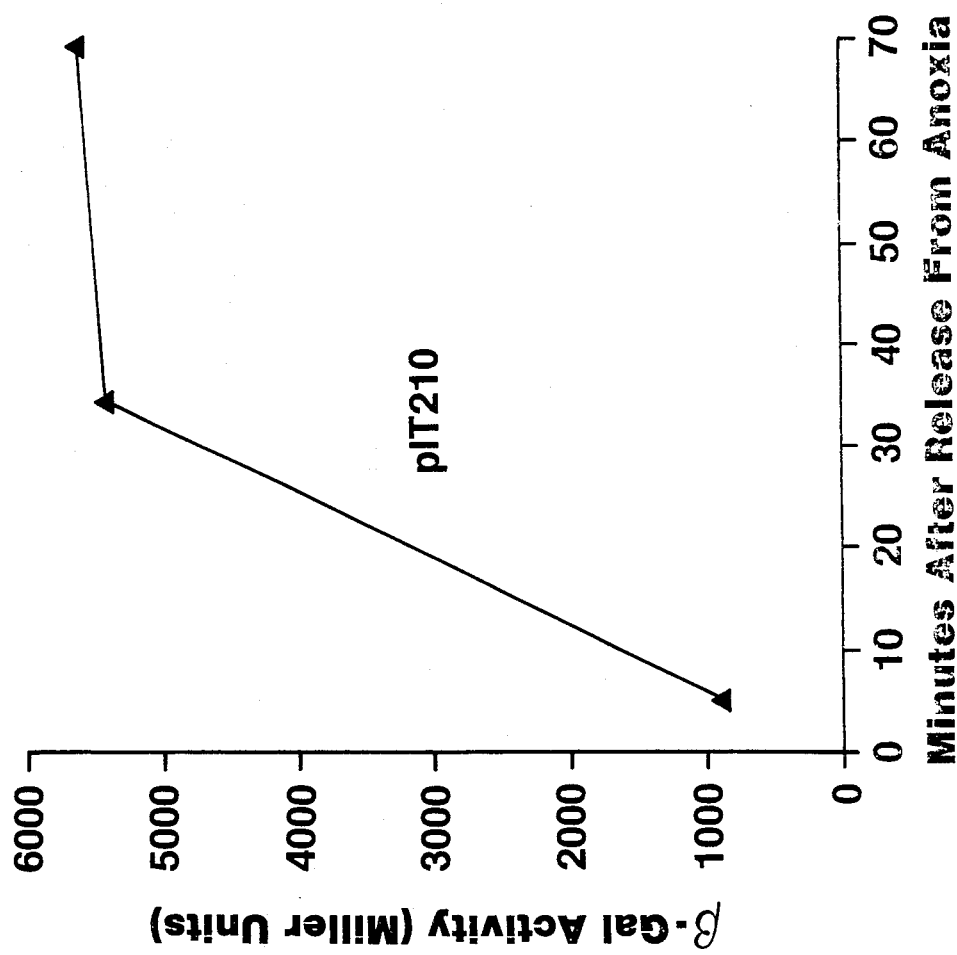
FIG. 3—effect of recovery from anoxia on induction of YG100 transcriptional and translational activating sequence.

About $5 \times 10^8$ of induced *Saccharomyces cerevisiae*/pIT120 cells were conventionally collected by centrifugation for 1 minute at 9,000×g. The cells were suspended in 2 ml of ice-cold breaking buffer (100 mM Tris-HCl, pH 7.5, 1 mM dithiothreitol and 1 mM phenylmethylsulfonylfluoride) to which 0.5 g of washed glass beads (450–500μ, washed with each of 10 ml 1N HCl and 30 ml of water per g of beads, and baked at 140° C. for 4 hours) were added. The cooled mixture was then sonicated with two 30 second bursts at full power using a conventional sonicator. The resultant cellular debris was conventionally removed by centrifugation for 1 minute and the protein concentration determined using the Coomassie Blue binding method (Bradford, 1976, Anal. Biochem. 72:248). Beta-galactosidase activity was calculated according to the method of Miller, 1972 Experiments in Molecular Genetics, Cold Spring Harbor Press, Cold Spring Harbor, N.Y. The results of induced expression of beta-galactosidase activity are presented in FIG. 3 of the accompanying drawings.

EXAMPLE 5

Construction of Integrative Plasmid pIT2100, *E. coli* K12 JA221/pIT2100 and *Saccharomyces cerevisiae*/pIT2100

A. Construction of the ~6.9 kb SmaI-SalI Fragment of Plasmid pIT210

About 5 μl (5 μg) of plasmid pIT210 in TE buffer, 5 μl DTT (100 mM Dithiothreitol), 5 μl (1000 mg/ml) BSA (bovine serum albumin), 25 μl water, 5 μl (5 units) SmaI restriction enzyme and 5 μl 10X reaction mix* are incubated at 37° C. for about 1 hour. The reaction is terminated by incubation at 70° C. for 5 minutes. After cooling on ice, about 1.5 μl of 5 M NaCl, and 2.5 μl (5 units) SalI restriction enzyme are added followed by incubation at 37° C. for 1 hour. The reaction is terminated, cooled on ice, extracted with each of phenol and chloroform:isoamyl alcohol (24:1) and then ethanol precipitated. The desired ~6.9 kb SmaI-SalI restriction fragments are conventionally separated and isolated by agarose gel electrophoresis (Maniatis et al, 1982). The desired ~6.9 kb fragments are dissolved in about 20 μl of TE buffer and stored at 0° C.

\* Reaction mix (10X) for SmaI restriction enzyme is prepared with the following composition:
200 mM KCl
100 Tris-HCl, pH 8.0
100 MgCl$_2$

B. SmaI-SalI Digestion of Plasmid YIp26

YIp26 is a yeast *E. coli* dual vector which contains the yeast URA3 and LEU2 genes as well as a prokaryotic ampicillin resistance gene. YIp26 does not contain information required for autonomous replication in yeast and therefore will stably transform yeast to leucine or uracil prototrophy only if the vector integrates into the yeast chromosomal DNA. YIp26 contains single recognition sites for SmaI and SalI restriction enzymes which facilitates the subcloning of DNA from pIT210.

The desired digestion is carried out in substantial accordance with the teaching of Example 5A except that plasmid YIp26 (ATCC 37057), rather than plasmid pIT120, is used. The desired digest is conventionally extracted, ethanol precipitated, dissolved in about 20 μl of TE buffer and then stored at 0° C. for future use.

Ligation and Construction of *E. coli* K12 JA221/pIT2100

The desired ligation and construction are carried out in substantial accordance with the teaching of Example 1E except that the fragments of Examples 5A and 5B, rather than plasmid pIT210, are used. The desired transformant is selected for ampicillin resistance, conventionally identified, characterized and cultured (See Example 7E), and then used to isolate plasmid pIT2100 in substantial accordance with the procedure of Example 1A.

D. Construction of *Saccharomyces cerevisiae*/pIT2100

About 10 μg of plasmid pIT2100 is digested in substantial accordance with the teaching of Example 1D except that NcoI restriction enzyme and reaction mix*, rather than BamHI restriction enzyme and reaction mix, are used. Linearizing the plasmid increases the efficiency with which the DNA integrates into the yeast chromosome and the linear ends target the plasmid to homologous sequences. Since the NcoI site of plasmid pIT2100 is within the URA3 gene, the plasmid integrates predominantly at the ura3 locus.

*Saccharomyces cerevisiae* DBY746 (ATCC 44773) is transformed with the linearized plasmid pIT2100 DNA in substantial accordance with the teaching of Example 2. Leucine prototrophs are selected. The transformants are checked for stability of the leucine prototrophy by growing the cells for about thirty generations without selection and then checking the percentage of cells retaining leucine prototrophy. An integrated copy of the LEU2 gene is greater than 90% stable over 30 generations whereas an autonomously replicating plasmid containing ARS sequences from 2 micron DNA or the yeast genome is less than 50% stable under these conditions.

*Reaction mix (10X) for NcoI restriction enzyme is prepared with the following composition:
1500 mM NaCl
100 mM Tris-HCl, pH 7.5
100 mM MgCl$_2$

EXAMPLE 6

Incubation of *Saccharomyces cerevisiae*/pIT2100 Under Anaerobic and Aerobic Conditions and Measurement of Beta-Galactosidase Activity The desired incubation, induction and measurement procedures are carried out in substantial accordance with the teaching of Examples 3 and 4 except that *Saccharomyces cerevisiae*/pIT2100, rather than *S. cerevisiae*/pIT210, is used.

EXAMPLE 7

Construction of Plasmid pIT2210 and *E. coli* K12 JA221/pIT2210

A. Isolation of the ~209 bp (base pair) XbaI-TaqI Fragment of Plasmid pIT120

About 500 μg of plasmid pIT120 is reacted in a total volume of 2 mls in 0.1 M Tris-HCl, pH7.5, 50 mM NaCl, 5 mM MgCl$_2$, 100 μg/ml bovine serum albumin and 500 units of EcoRI and XbaI restriction enzymes until digestion is complete. The 365 bp (plus 4b 5' extension on each strand) XbaI-EcoRI fragment is then isolated from an acrylamide gel and purified using standard procedures (Schleif and Wensink, 1981. Practical Methods in Molecular Biology, Springer-Verlag, New York, N.Y.). About 20 μg of this fragment is then reacted with 2 units of TaqI restriction enzyme in 200 μl of 0.01 M Tris-HCl, pH8.4, 0.1 M NaCl 0.006 M MgCl$_2$, 0.006 M 2-mercaptoethanol and 100 μg/ml bovine serum albumin at 65° C. under paraffin oil. Every hour for 5 hours a 40 μl aliquot is removed and quenched in phenol. The aliquots are pooled, purified using standard procedures (Schleif and Wensink, 1981) and electrophoresed on acrylamide. The products of the partial TaqI digestion will be the desired XbaI-TaqI fragment of 209 bp (plus a 4b and a 2b 5' extension), a XbaI-TacI fragment of 167 bp (plus a 4b and a 2b 5' extension), the full length XbaI-EcoRI fragment of 365 bp (plus 4b 5' extensions on each strand), an EcoRI-TaqI fragment of 137 bp (plus a 2b and a 4b 5' extension) a EcoRI-TaqI fragment of 179 bp (plus a 4b and a 2b 5' extension), and a TaqI-TaqI fragment of 41bp (plus a 2b 5' extension on each strand). The desired ~209 bp fragment is conventionally isolated from an acrylamide gel and purified.

B. Construction of the Linker Sequence

```
CGAGAAGGGATTGAGTTGTAGTTTCGTTTCCCAATTCTTAC
||||||||||||||||||||||||||||||||||||||||
TCTTCCCTAACTCAACATCAAAGCAAAGGGTTAAGAATG

TTAAGTTGTTTTATTTTCTCTATTTGTAAGATAAGCACATC
||||||||||||||||||||||||||||||||||||||||
AATTCAACAAAATAAAAGAGATAAACATTCTATTCGTGTAG

AAAAGAAAAGTAATCAAGTATTACAAGAAACAAAAATTCAA
||||||||||||||||||||||||||||||||||||||||
TTTTCTTTTCATTAGTTCATAATGTTCTTTGTTTTAAGTT

GTAAATAACAGATAATATGTTCGTTAACCAACACTTGT
||||||||||||||||||||||||||||||||||||
CATTTATTGTCTATTATACAAGCAATTGGTTGTGAAC
``` wherein
A is deoxyadenyl,
G is deoxyguanyl,
C is deoxycytosyl and
T is thymidyl.

The desired DNA is conventionally synthesized by the modified phosphotriester method using fully protected trideoxyribonucleotide building blocks in substantial accordance with the methods of Itakura et al., 1977, Science 198:1056 and Crea et al., 1978, Pro. Nat. Acad. Sci. USA 75:5765. The linker is then dissolved in 50 μl of TE buffer and stored at 0° C. for further use.

C. Isolation of the ~253 bp HphI-BamHI Fragment of Plasmid pNM587.4-4

About 100 μg of plasmid pNM587.4-4 (NRRL B-15812) is reacted at 37° C. in a total volume of 1 ml with 100 units HphI restriction enzyme in 6 mM KCl, 10 mM Tris-HCl, pH7.4, 10 mM MgCl$_2$, 1 mM dithiothreitol and 200 μg/ml bovine serum albumin. When digestion is complete, 30 μl of 5 M NaCl is added followed by 100 units of BamHI restriction enzyme. Incubation at 37° C. is continued until the second digestion is complete. The desired 253 bp (plus a 4b 5' extension and a 1b 3' extension) HphI-BamHI fragment is purified from acrylamide using standard procedures. The fragment comprises the human proinsulin gene except for the N-terminal six amino acid codons.

D. Isolation of the XbaI-BamHI Fragments of Plasmid pIT120

About 10 μg of plasmid pIT120 is reacted at 37° C. in a total volume of 100 μl with 20 units each of XbaI and BamHI restriction enzymes in 150 mM NaCl, 6 mM Tris-HCl, pH7.9, 6 mM MgCl$_2$ and 100 μl/ml bovine serum albumin. When digestion is complete, the DNA is purified with phenol and chloroform and ethanol precipitated using standard procedures.

E. Ligation and Transformation

About 1 μg of each of the purified fragments of Examples 7A, B and C and about 1 μg of the DNA of Example 7D are mixed in a total volume of 30 μl in 50 mM Tris-HCl, pH7.8, 10 mM MgCl$_2$, 20 mM dithiothrietol, 1 mM ATP and 50 μg/ml bovine serum albumin. About 100 units of T4 DNA ligase is then added followed by incubation at 4° C. for about 16 hours. The ligation mixture is used to transform *E. coli* K12 JA221 and transformants are selected on ampicillin plates. Clones containing the desired DNA fragments are identified by using colony hybridization (with the nick translated purified fragments from Examples 7A, B and C as probes) and structural analysis after isolating small amounts of DNA. The desired recombinant will have the fragments from Examples 7A, B, and C ligated in order into the XbaI and BamHI sites of plasmid pIT120. The resultant *E. coli* K12 JA221/pIT2210 transformant serves as a preferred source of plasmid pIT2210.

EXAMPLE 8

Construction of plasmid pIT3210 and E. coli K12 JA221/pIT3210

A. Isolation of ~1,600 bp Fragment of Plasmid PIT2210

About 20 μg of plasmid pIT2210 is reacted at 37° C. in a total volume of 200 μl with 20 units of each of BamHI and BglII restriction enzymes in 60 mM NaCl, 10 mM Tris-HCl, pH 7.5, 6 mM MgCl$_2$ and 1 μg/ml bovine serum albumin. When digestion is complete, the DNA is purified with phenol and chloroform and then ethanol precipitated using standard procedures. The desired ~1,600 bp fragment is conventionally isolated from an acrylamide gel and purified.

B. BamHI Digestion of Plasmid YEp24

The desired digestion is carried out in substantial accordance with the teaching of Example 1D except that plasmid YEp24, rather than plasmid pMC1587, is used. The resultant BamHI digest is conventionally extracted, ethanol precipitated and dissolved in TE buffer without further purification.

C. Ligation and Transformation

About 1 μg each of the ~1,600 bp fragment of plasmid pIT2210 and the BamHI digest of plasmid YEp24 are ligated in substantial accordance with the teaching of Example 7E. The ligated DNA is used to transform E. coli K12 JA221 in substantial accordance with the teaching of Example 1E. Desired clones are identified by colony hybidization and DNA structural analysis as previously described (Example 7E). The resultant E. coli K12 JA221/pIT3210 transformants serve as a preferred source of plasmid pIT3210. Plasmid pIT3210 replicates and is selectable in E. coli and yeast since YEp24 contains the origin of replication and ampicillin resistance gene of pBR322, the URA3 gene from yeast and a replication sequence from the yeast 2 micron plasmid. The above procedure also generates an isomeric form of plasmid pIT3210. The isomer results because the ~1,600 bp BamHI-BglII fragment of pIT2210 can be ligated into the BamHI-digested plasmid YEp24 in either of two directions. The isomeric plasmids are conventionally isolated and identified by restriction enzyme analysis. A restriction site map of plasmid pIT3210 is presented in FIG. 1 of the accompanying drawings.

EXAMPLE 9

Construction of Saccharomyces cerevisiae/pIT3210

The desired construction is made in substantial accordance with the teaching of Example 2 except that plasmid pIT3210, rather than plasmid pIT210, is used. The resultant colonies are conventionally cultured and constitute the desired Saccharomyces cerevisiae/pIT3210 transformants.

EXAMPLE 10

Incubation of Saccharomyces cerevisiae/pIT3210 Under Anaerobic and Aerobic Conditions and Induced Expression of Human Methionyl Proinsulin The incubation is carried out in substantial accordance with the teaching of Example 3 except that Saccharomyces cerevisiae/pIT3210, rather than S. cerevisiae/pIT210, is used. The resultant induction of the YG100 gene transcriptional and translational activating sequence results in high level expression of human methionyl proinsulin. The desired proinsulin product is conventionally isolated by preparative HPLC and identified by radioimmunoassay and other tests.

We claim:

1. A method for inducing a high level expression in yeast of a nucleotide sequence that is under the transcriptional and translational control of the yeast YH100 gene, said method comprising
   (1) transforming a yeast cell with selectable plasmid that is capable of autonomous replication or genomic integration, said plasmid comprising, in translational reading frame,
      (a) the transcriptional and translational activating sequence of the yeast YG100 gene, and
      (b) a nucleotide sequence that codes for a functional heterologous polypeptide,
   (2) culturing said transformed cell under conditions suitable for aerobic growth,
   (3) culturing said aerobically-grown cells under conditions suitable for anaerobic growth, and
   (4) culturing said anaerobically-grown cells under conditions suitable for aerobic growth and gene expression,
   subject to the limitation that said conditions for anaerobic growth are maintained for a time sufficient to cause induction of the transcriptional and translational activating sequence of the yeast YG100 gene when said conditions for aerobic growth are restored.

2. The method of claim 1 wherein prior to culturing under conditions suitable for anaerobic growth, said transformed cell is cultured under conditions suitable for aerobic growth until about mid-logarithmic growth phase and wherein conditions suitable for anaerobic growth are maintained for about 12 hours to at or near stationary growth phase.

3. The method of claim 2 wherein the nucleotide sequence codes for bovine growth hormone or bovine pre-growth hormone.

4. The method of claim 2 wherein the selectable plasmid is capable of genomic integration.

5. The method of claim 2 wherein the nucleotide sequence that codes for a functional polypeptide is selected from the group consisting of sequence that code for bovine growth hormone, bovine pre-growth hormone, human growth hormone, human pre-growth hormone, porcine growth hormone, mammalian growth hormone, avian growth hormone, growth hormone releasing factor, human insulin A chain, human insulin B chain, human proinsulin, human pre-proinsulin, human and non-human interferon, urokinase, tissue plasminogen activator, interleukin I, interleukin II, beta-galactosidase, any hormone, any enzyme and any biactive polypeptide.

6. The method of claim 5 wherein the nucleotide sequence that codes for a functional polypeptide is selected from the group consisting of sequences that code for beta-galalctosidase and human proinsulin.

7. The method of claim 2 in which the plasmid is pIT210.

8. The method of claim 2 in which the plasmid is pIT2100.

9. The method of claim 2 in which the plasmid is pIT3210.

10. The method of claim 2 wherein the yeast cell is Saccharomyces.

11. The method of claim 2 wherein the transformed yeast cell is *Saccharomyces cerevisiae*.

12. The method of claim 2 wherein the transformed yeast cell is *Saccharomyces cerevisiae* DBY 689/pIT210.

13. The method of claim 2 wherein the transformed yeast cell is *Saccharomyces cerevisiae* DBY689/pIT3210.

14. A method for inducing high level expression in yeast of a nucleotide sequence that is under the transcriptional and translational control of the yeast YG100 gene, said method comprising culturing a tranformed yeast cell at or near stationary growth phase under conditons suitable for growth and gene expression, said transformed yeast cell comprising the selectable plasmid of claim 1.

15. The method of claim 10 wherein the nucleotide sequence that codes for a functional polypeptide is selected from the group consisting of sequences that code for bovine growth hormone, bovine pre-growth hormone, human growth hormone, human pre-growth hormone, procine growth hormone, mammalian growth hormone, avian growth hormone, growth hormone releasing factor, human insulin A chain, human insulin B chain, human proinsulin, human pre-proinsulin, human and non-human interferon, urokinase, tissue plasminogen activator, interleukin I, interleukin II, beta-galactosidase, any hormone, any enzyme and any bioactive polypeptide.

16. The method of claim 15 wherein the nucleotide sequence that codes for a functional polypeptide is selected from the group consisting of sequences that code for beta-galactosidase and human proinsulin.

17. The method of claim 10 wherein the selectable plasmid is capable of genomic integration.

18. The method of claim 10 in which the plasmid is pIT210.

19. The method of claim 10 in which the plasmid is pIT2100.

20. The method of claim 10 in which the plasmid is pIT3210.

21. The method of claim 10 wherein the yeast cell is Saccharomyces.

22. The method of claim 10 wherein the yeast cell is *Saccharomyces cerevisiae*.

23. The method of claim 10 wherein the yeast cell is *Saccharomyces cerevisiae* DBY689/pIT210.

24. The method of claim 10 wherein the yeast cell is *Saccharomyces cerevisiae* DBY746/pIT3210.

25. The method of claim 1 wherein said tranformed cell is cultured at or near stationary growth phase prior to culturing under conditions suitable for anaerobic growth.

26. The method of claim 1 wherein said anaerobically-grown cells are cultured at or near stationary growth phase under conditons suitable for aerobic growth and gene expression.

27. The method of claim 1 wherein the culture temperature for aerobic and anaerobic growth is about 37° C.

28. The method of claim 2 wherein the culture temperature for aerobic and anaerobic growth is about 37° C.

29. The method of claim 17 wherein the culture temperature for aerobic and anaerobic growth is about 37° C.

30. The method of claim 18 wherein the culture temperature for aerobic and anaerobic growth is about 37° C.

31. The method of claim 22 wherein the selectable DNA is plasmid PIT210.

32. A selectable plasmid that is capable of autonomous replication or genomic integration, said plasmid comprising, in translational reading frame,
    (a) the transcriptional and translational activating sequence of the yeast YG100 gene, and
    (b) a nucleotide sequence that codes for a functional heterologous polypeptide.

33. The selectable plasmid of claim 24 which is plasmid pIT210.

34. The selectable plasmid of claim 24 which is plasmid pIT2100.

35. The selectable plasmid of claim 24 which is plasmid pIT3210.

36. The transformed yeast cell of claim 1 which is Saccharomyces.

37. The transformed yeast cell of claim 1 which is *Saccharomyces cerevisiae*.

38. The transformed yeast cell of claim 1 which is *Saccharomyces cerevisiae*/pIT3210.

39. The transformed yeast cell of claim 1 which is *Saccharomyces cerevisiae* DBY689/pIT3210.

40. A method for inducing high level expression in yeast of a nucleotide sequence that is under the transcriptional and translational control of the yeast YG100gene, said method comprising culturing a yeast cell transformed with the selectable plasmid of claim 32 under anaerobic conditions until late or stationary growth phase and then culturing said anaerobically grown cells under conditions suitable for aerobic growth and gene expression.

41. The method of claim 40 wherein the culture temperature for anaerobic and aerobic growth is about 37° C.

* * * * *

UNITED STATES PATENT AND TRADEMARK OFFICE
CERTIFICATE OF CORRECTION

PATENT NO. : 4,745,057

DATED : May 17, 1988

INVENTOR(S) : Cheryl A. Beckage and Thomas D. Ingolia

It is certified that error appears in the above-identified patent and that said Letters Patent is hereby corrected as shown below:

Column 7, line 29 - "desired µl.3" should be --desired ∿1.3--

Column 10, line 28 - The letter "C" needs to be inserted in the title before "Ligation"

Column 11, line 37 - "XbaI-TacI" should be --Xbal-Taql--

Column 14, Claim 1, line 8 - "YH100" should be --YG100--

Column 14, Claim 5, line 46 - "sequence" should be --sequences--

Column 14, Claim 5, line 56 - "biactive" should be --bioactive--

Column 15, Claim 14, line 12 - conditons" should be --conditions--

Column 16, Claim 26, line 3 - "conditons" should be --conditions--

UNITED STATES PATENT AND TRADEMARK OFFICE
CERTIFICATE OF CORRECTION

PATENT NO. : 4,745,057

DATED : May 17, 1988

INVENTOR(S) : Cheryl A. Beckage and Thomas D. Ingolia

It is certified that error appears in the above-identified patent and that said Letters Patent is hereby corrected as shown below:

Column 16, Claim 40, line 43- "YG100gene" should be --YG100 gene--

Signed and Sealed this

Fourth Day of February, 1992

*Attest:*

HARRY F. MANBECK, JR.

*Attesting Officer*      *Commissioner of Patents and Trademarks*